(12) United States Patent
Bigolin et al.

(10) Patent No.: US 12,734,757 B2
(45) Date of Patent: Sep. 15, 2026

(54) METHOD FOR THE REALIZATION OF A SUPPORT ELEMENT FOR THE HUMAN BODY AND A SUPPORT ELEMENT SO OBTAINED

(71) Applicant: SELLE ROYAL GROUP S.p.A., Pozzoleone (IT)

(72) Inventors: Barbara Bigolin, Pozzoleone (IT); Marco Malfatti, Pozzoleone (IT)

(73) Assignee: SELLE ROYAL GROUP S.P.A., Pozzoleone (IT)

( * ) Notice: Subject to any disclaimer, the term of this patent is extended or adjusted under 35 U.S.C. 154(b) by 402 days.

(21) Appl. No.: 18/279,473

(22) PCT Filed: Mar. 4, 2022

(86) PCT No.: PCT/IB2022/051911
§ 371 (c)(1),
(2) Date: Aug. 30, 2023

(87) PCT Pub. No.: WO2022/185262
PCT Pub. Date: Sep. 9, 2022

(65) Prior Publication Data

US 2024/0140035 A1 May 2, 2024

(30) Foreign Application Priority Data

Mar. 4, 2021 (IT) ........................ 102021000005111

(51) Int. Cl.
*B29C 64/386* (2017.01)
*A61B 5/103* (2006.01)
(Continued)

(52) U.S. Cl.
CPC .......... *B29C 64/386* (2017.08); *A61B 5/1036* (2013.01); *B33Y 10/00* (2014.12);
(Continued)

(58) Field of Classification Search
CPC .......... A61B 5/6826; A61B 2562/0219; A61B 2562/0247; A61B 2562/046;
(Continued)

(56) References Cited

U.S. PATENT DOCUMENTS

2007/0245504 A1* 10/2007 Spector .................. B33Y 50/00 73/172
2011/0115265 A1* 5/2011 Scheffer .................. B62J 1/007 297/204
(Continued)

OTHER PUBLICATIONS

International Search Report for PCT/IB2022/051911 dated Nov. 25, 2022 (3 pages).
(Continued)

*Primary Examiner* — Daniel Previl
(74) *Attorney, Agent, or Firm* — Tutunjian & Bitetto, P.C.

(57) ABSTRACT

A method for making a support element for the human body equipped with a first component or support component, a second component or padding component, wherein at least the second component or padding component is obtained by means of a three-dimensional printing technique; and an apparatus for implementing the method for obtaining the support element and support element thus obtained.

27 Claims, 8 Drawing Sheets

(51) Int. Cl.

| | |
|---|---|
| ***B33Y 10/00*** | (2015.01) |
| ***B33Y 30/00*** | (2015.01) |
| ***B33Y 50/00*** | (2015.01) |
| ***B33Y 80/00*** | (2015.01) |
| ***B62J 1/00*** | (2006.01) |
| ***B62J 1/02*** | (2006.01) |
| ***B62K 21/26*** | (2006.01) |
| *B29L 31/30* | (2006.01) |
| *B29L 31/46* | (2006.01) |
| *B29L 31/60* | (2006.01) |

(52) U.S. Cl.

CPC ............... *B33Y 30/00* (2014.12); *B33Y 50/00* (2014.12); *B33Y 80/00* (2014.12); *B62J 1/007* (2013.01); *B62J 1/02* (2013.01); *B62K 21/26* (2013.01); *B29K 2995/0091* (2013.01); *B29L 2031/3094* (2013.01); *B29L 2031/463* (2013.01); *B29L 2031/608* (2013.01)

(58) Field of Classification Search

CPC ... A61B 5/0006; A61B 5/0008; A61B 5/0013; A61B 5/002; A61B 5/0022; A61B 5/0051; A61B 5/0077; A61B 5/01; A61B 5/02055; A61B 5/0261; A61B 5/053; A61B 5/1036; A61B 5/11; A61B 5/1112; A61B 5/1116; A61B 5/1117; A61B 5/1118; A61B 5/318; A61B 5/369; A61B 5/384; A61B 5/389; A61B 5/395; A61B 5/4381; A61B 5/6803; A61B 5/6806; A61B 5/6807; A61B 5/681; A61B 5/6824; A61B 5/6838; A61B 5/6847; A61B 5/6891; A61B 5/7264; A61B 7/00; A61B 7/04; A61B 7/045; A61B 8/00; A61B 8/06; A61B 8/0808; A61B 8/4427; A61B 8/488; A61B 8/565; A61B 6/00; A61B 10/00; A61B 16/00; G06N 20/00; G06N 3/006; G06N 5/022; G06N 5/048; G06N 3/00; G06N 5/00; A43B 3/42; A43B 3/46; A43B 3/48; B29C 64/386; B29C 63/18; B29C 31/00; B29C 33/00; B29C 35/00; B29C 37/00; B29C 39/00; B29C 41/00; B29C 43/00; B29C 44/00; B29C 45/00; B29C 48/00; B29C 57/00; B29C 59/00; B29C 61/00; B29K 2995/0091; B29L 2031/3094; B29L 2031/463; B29L 2031/608; B29L 2023/00; B29L 2031/3047; B29L 2031/3091; B29L 2001/00; B29L 2005/00; B29L 2007/00; B29L 2009/00; B29L 2011/00; B29L 2012/00; B33Y 10/00; B33Y 30/00; B33Y 50/00; B33Y 80/00; B62J 1/00; B62J 1/007; B62J 1/02; B62J 1/18; B62J 1/26; B62K 21/26; B62K 21/14; B62K 21/16; B62K 21/12; B62K 1/00; B62K 3/00; B62K 5/00; B62K 7/00; B62K 9/00; B62K 11/00; B62K 13/00; B62K 15/00; B62K 17/00; B62K 19/00; B62K 21/00; B62K 23/00; B62K 27/00; B62K 25/00; B62K 2201/00; B62K 2202/00; B62K 2204/00; B62K 2206/00; G06F 15/76; G06F 16/2282; G06F 16/288; G08B 21/02; G08B 21/0423; G08B 21/0446; G08B 21/0453; G08B 21/0461; G08B 21/0476; G08B 21/0484; G08B 21/0492; G08B 25/016; G16H 15/00; G16H 20/13; G16H 20/30; G16H 40/67; G16H 50/20; G16H 80/00; G16Z 99/00; H04M 2250/12; H04M 3/5116; H04W 84/18; H04W 4/00; H04W 8/00; H04W 12/00; H04W 16/00; H04W 99/00; H04W 92/00; H04W 88/00; H04W 84/00; H04W 80/00; H04W 76/00; H04W 74/00; H04W 72/00; H04W 68/00; H04W 64/00; H04W 60/00; H04W 56/00; H04W 52/00; H04W 48/00; H04W 40/00; H04W 36/00; H04W 28/00; H04W 24/00; Y10T 74/20786; Y10T 74/2078; Y10T 74/20792; Y10T 74/20798; Y10T 74/20828; Y10T 29/53652; Y10T 29/53657; Y10T 29/4981; Y10T 29/4987; Y10T 74/20804; Y10T 74/2087; Y10T 24/00; Y10T 29/00; Y10T 70/00; Y10T 74/00; Y10T 82/00; Y10T 83/00; Y10T 117/00; Y10T 137/00; Y10T 152/00; Y10T 156/00; Y10T 225/00; Y10T 279/00; Y10T 292/00; Y10T 403/00; Y10T 407/00; Y10T 408/00; Y10T 409/00; Y10T 428/00; Y10T 436/00; Y10T 442/00; Y10T 464/00; Y10T 483/00; A41D 19/0024; A41D 19/01547; A41D 19/0157; A41D 19/01588; A41D 2600/102; A41D 2600/104; A41D 1/00; A41D 3/00; A41D 5/00; A41D 7/00; A41D 10/00; A41D 11/00; A41D 13/00; A41D 15/00; A41D 17/00; A41D 19/00; A41D 20/00; A41D 23/00; A41D 25/00; A41D 27/00; A41D 29/00; A41D 31/00; A41D 2200/00; A41D 2300/00; A41D 2400/00; A41D 2500/00; A41D 2600/00; A63B 71/143; A63B 1/00; A63B 3/00; A63B 4/00; A63B 5/00; A63B 6/00; A63B 7/00; A63B 9/00; A63B 15/00; A63B 17/00; A63B 19/00; A63B 21/00; A63B 22/00; A63B 23/00; A63B 24/00; A63B 25/00; A63B 26/00; A63B 27/00; A63B 29/00; A63B 31/00; A63B 33/00; A63B 35/00; A63B 37/00; A63B 39/00; A63B 41/00; A63B 43/00; B25D 17/043; B25D 1/00; B25D 3/00; B25D 5/00; B25D 7/00; B25D 9/00; B25D 2222/00; B25D 2250/00; B25D 2217/00

USPC ..... 340/427, 432, 426.16, 426.22, 438, 439, 340/902, 903, 904, 925, 959–960, 464, 340/995.12, 995.17

See application file for complete search history.

(56) References Cited

U.S. PATENT DOCUMENTS

| | | | | |
|---|---|---|---|---|
| 2018/0228401 | A1* | 8/2018 | Schwartz ................. | A43D 1/02 |
| 2020/0079452 | A1* | 3/2020 | Shabsigh ................. | B62J 1/005 |

OTHER PUBLICATIONS

Singhal et al., "3D-Printed Sole with Variable Density using Foot Plantar Pressure Measurements", 2018 IEEE 8th International Advance Computing Conference (IACC), Dec. 14, 2018, pp. 1-7.

Dev Nath et al., "An Overview of Additive Manufacturing of Polymers and Associated Composites", Polymers, vol. 12, No. 11, Nov. 17, 2020, pp. 1-33.

* cited by examiner 3
10
6
5
2
13
17

100
108
107
105
102
104
102b
106
109
103

103
100
102
102a 108
103

108
100

METHOD FOR THE REALIZATION OF A SUPPORT ELEMENT FOR THE HUMAN BODY AND A SUPPORT ELEMENT SO OBTAINED

TECHNICAL FIELD OF THE INVENTION

The present invention relates to a method for manufacturing a support element for the human body, such as for example a saddle of a bicycle or of a vehicle in general, a grip for a handlebar of a bicycle or of a vehicle in general, a shock-absorbing element (or suspension element, the so-called "elastomer") for a saddle or seat for the human body, which allows to obtain a support element that adapts to the anatomical or other needs of the user.

The present invention is also directed to a support element obtained with this method, as well as to an apparatus capable of implementing the method object of the present invention.

DESCRIPTION OF RELATED ART

The technologies that use three-dimensional (3D) printing techniques are undergoing an ever-wider diffusion, in different production sectors, of design and research in general.

The term 3D printing usually refers to the creation of three-dimensional objects having a various function and conformation, by means of an additive manufacturing technique starting from a three-dimensional digital model. The digital model can be obtained by means of a specific software and subsequently elaborated in order to be able to be realized through different technologies and/or through a 3D printer.

Also known are the support elements for the human body, which are usually composed of a first component or support component and a second elastic component or padding component.

These support elements very often have the disadvantage of being made in a standardized way, without the possibility of adapting to the specific, even anatomical, needs of the user. There is therefore a need to have a support element that can be easily modelled and/or customized in order to meet the various needs of the user, as well as a simple and rapid method for obtaining the same.

SUMMARY OF THE INVENTION

An object of the present invention is to overcome the drawbacks found above for the known art.

An object of the present invention is to provide a method for making a support for the human body that allows the personalization of the latter.

A further object of the present invention is to provide a method for making a support element which is fast and simple.

These purposes, as well as others which will become clearer later, are achieved by a method for manufacturing a support element for the human body according to the present application. A further object of the present invention is to provide an apparatus for making a support element for the human body, which allows to obtain a support element for the human body of a customized type, in a quick and simple way.

According to this aspect of the invention, an apparatus is provided in accordance with the present application.

A particular object of the present invention is to provide a support element for the human body, such as for example a bicycle saddle or a vehicle in general, a grip for a handlebar of a bicycle or a vehicle in general, a shock-absorbing element for a saddle or seat for the human body, a helmet for example for cycling, a pad for a cycling shorts, a sole for a sports and/or cycling shoe, etc., which can be customized on the basis of specific needs, including anatomical ones, of the user.

A further object of the present invention is to provide a support element for the human body capable of exhibiting high mechanical properties.

According to this aspect of the invention, a support element for the human body is provided in accordance with the present application.

The present application refers to preferred and advantageous embodiments of the invention.

BRIEF DESCRIPTION OF THE DRAWINGS

Other characteristics and advantages of the invention will be more evident from the description of an example of embodiment of a support element, illustrated by way of example in the accompanying drawings in which.

In the accompanying drawings, identical parts or components are indicated by the same reference numbers.

DETAILED DESCRIPTION

The present invention relates to a support element 1 for the human body, such as for example a saddle of a bicycle or of a vehicle in general, a grip for a handlebar of a bicycle or a vehicle in general, a shock-absorbing element (or suspension element, the so-called "elastomer") for a saddle or seat for the human body.

The present invention could also have as its subject an insert or element for absorbing shocks or impacts for a helmet, for example for cycling, a shock-absorbing insert placed for example between the support component and the padding component of a bicycle saddle or on top of the padding component, or on top of a possible covering element that covers the padding component, a pad-insert for a cycling shorts, a sole or an internal insole of a sports and/or cycling shoe, etc., made according to the present description, without any limitation.

Figures 5, 6, 7:
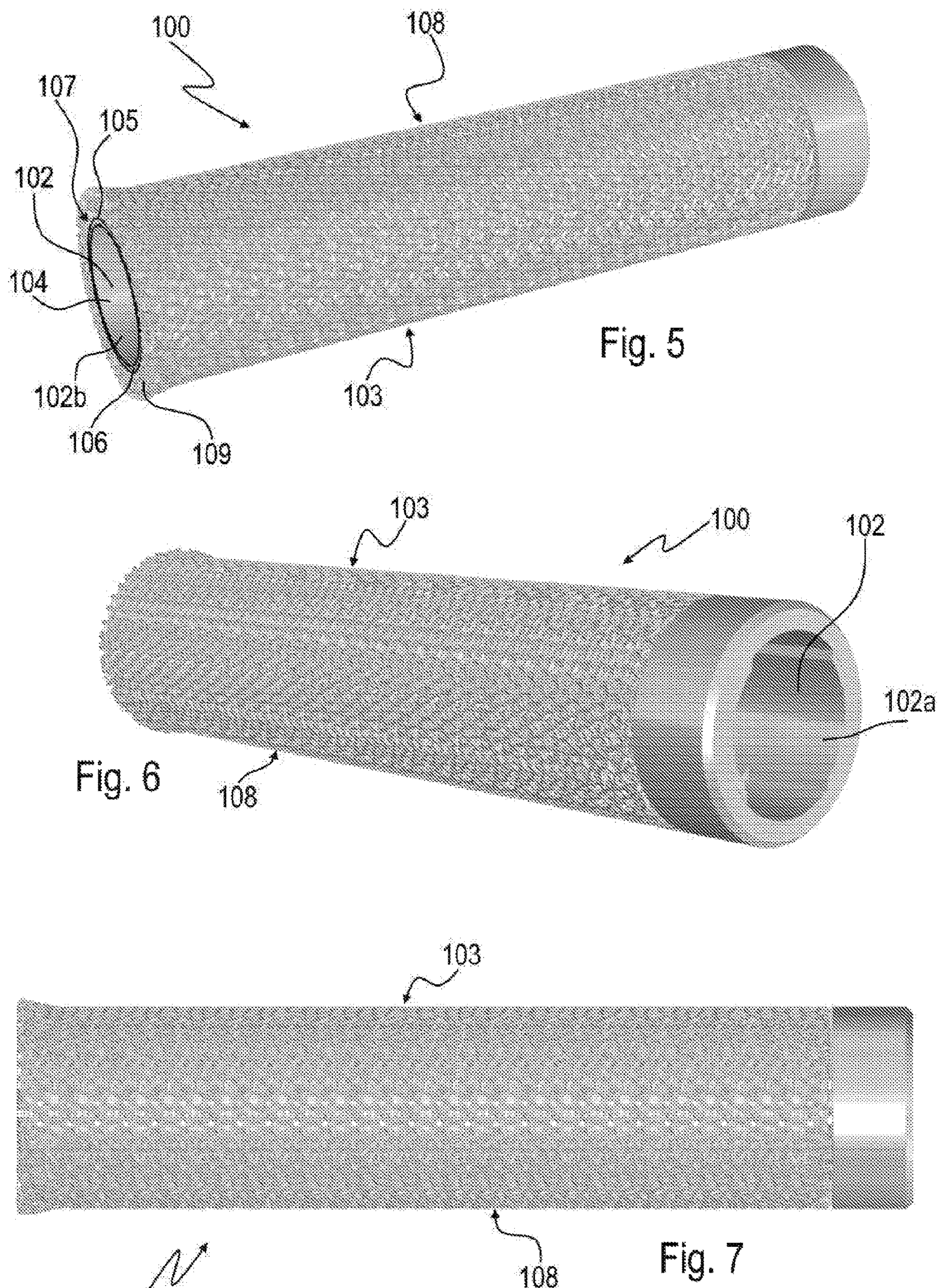
FIG. 5 is a side perspective view of a grip for a bicycle handlebar according to a version of the present invention.
FIG. 6 is a side perspective view of the grip shown in FIG. 5.
FIG. 7 is a side view of the grip shown in FIG. 5.
Figure 8:
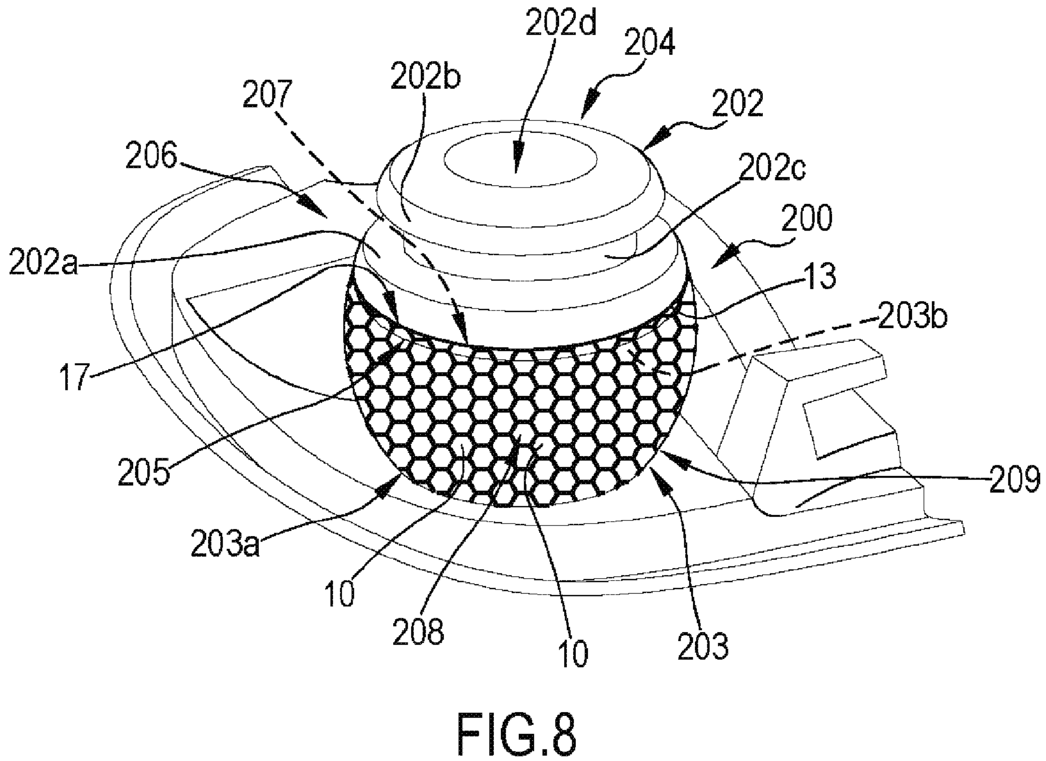
FIG. 8 is a slightly perspective side view of a further version of a support element according to the present invention, FIG. 9 schematically illustrates the steps of obtaining and manufacturing a support element according to a version of the present invention.

With reference to the aforementioned FIGS. 1 to 4, a support element 1 in the form of a bicycle saddle 1 is shown, in FIGS. 5 to 7 a support element 1 in the form of a grip 100 for a handlebar of a bicycle or of a vehicle is illustrated, finally FIG. 8 illustrates a support element 1 in the form of a shock-absorbing element (or suspension element, a so-called "elastomer") 200 for a saddle or seat for the human body.

In any case, the following description will not be limited to one of the variants indicated above, unless the contrary is explicitly indicated, and is intended to be applicable to all the support elements for the human body having the characteristics described.

In particular, the support element 1 comprises a first component or support component 2 and a second component or padding component 3.

In at least one version, the first component 2 is a support component and the second component is a padding component 3, supported by the first component 2.

The second component or padding component 3 constitutes the elastic and/or shock absorbing and/or comfort portion of the support element for the human body 1.

The first component or support component 2, on the other hand, constitutes the most rigid portion of the support element for the human body 1 and serves to support the weight of the user and/or to guarantee a rigid structure to the support element 1.

Thus, the first component or support component 2 is more rigid and less elastic than the second component or padding component 3. Consequently, the second component or padding component 3 is more elastic and less rigid than the first component or support component 2.

The support element for the human body 1 could also comprise a covering element, for example in the form of a film or thin layer made of a plastic material or a natural material, placed above and/or covering the second component or padding component 3. This covering element, which may not be present in at least one version of the invention, is not shown in the attached figures. The covering element may prevent dirt, dust or other particles, such as moisture or fluids, from getting inside the second component or padding component 3.

If, on the other hand, the covering element is not present, the structure of the support element 1 is such that it can be washed and/or rinsed, if necessary, easily and quickly to eliminate dirt, dust and other particles.

Furthermore, at least according to one version of the invention, the covering element can have the function of increasing the comfort of the support element. The second component or padding component 3, in fact, could have a structure such as not to guarantee a comfortable support surface for the support element 1 and therefore the presence of the covering element could obviate this drawback and restore comfort for the support of the human body.

According to at least one version of the present invention, the covering element, if present, constitutes the contact surface with the human body while, if absent, it will be the second component or padding component 3 that can constitute the contact surface with the human body.

In any case, the second component or padding component 3 is fixed and/or adhered to and/or constrained to a first surface 4 of the first component or support component 2. The first component or support component 2 also comprises a second surface 5, opposite the first surface 4 and has a thickness 6, given by the distance between the first surface 4 and the second surface 5.

Similarly, the second component or padding component 3 has an internal surface 7 capable of coming into contact and/or being fixed and/or adhered to and/or constrained to the first surface 4 of the first component or support component 2, an external surface 8 opposite to the internal surface 7 and suitable, if present, to come into contact and/or to be covered by the covering element described above.

In one version of the invention, the external surface 8 could constitute the contact surface with the human body.

The second component or padding component 3 also has a thickness 9 given by the distance between the internal surface 7 and the external surface 8.

The second component or padding component 3, in at least one version of the invention, can have an extension substantially corresponding to or slightly higher or slightly lower than the extension of the first surface 4 of the first component or support component 2.

The support element 1 for the human body, or its first component or support component 2 and/or its second component or padding component 3 is made by means of three-dimensional printing.

Going into more detail, the second component or padding component 3 is, in at least one version, composed of a plurality of cells 10. The second component or padding component 3, therefore, has a honeycomb structure, formed by this plurality of cells 10. In one version of the invention, the second component or padding component 3 consists exclusively of this honeycomb structure, formed by the plurality of cells 10.

Each cell 10 can have a polyhedral and/or parallelogram shape or any other shape defined according to the needs of the end user and/or the manufacturer.

Each cell 10 has a substantially three-dimensional structure or conformation, formed by a plurality of faces.

Each face has a substantially parallelepiped or polygonal conformation, for example a triangle, square or rectangle, hexagon, pentagon, octagon, etc.

According to a further version of the invention, each cell can have a gyroid conformation. This type of cell 10 can bring advantages in terms of weight and thickness of the second component or padding component 3.

Furthermore, it is possible that such a cell conformation 10 determines a non-continuous and/or bumpy and/or wavy resting surface of the human body. In the event that this surface is uncomfortable for the human body to rest, it could be covered with a covering element so as to obviate this drawback.

The dimensions and/or the conformation of the various faces of the cells 10 can vary, depending on whether the face in question is positioned externally, internally, laterally and/or substantially perpendicular to the first component or support component 2.

A characteristic of at least one version of the present invention is that the plurality of cells 10, which constitutes the second component or padding component 3, has the outermost cells 10 (i.e. placed in an opposite position with respect to the first component or support component 2) with their outermost face substantially coplanar with each other. In this way, the outer faces of the outermost cells 10 constitute the external surface 8 of the second component or padding component 3 or the surface in contact with the user.

In at least one version of the present invention, the plurality of cells 10 is arranged according to at least one layer or according to at least a pair of layers superimposed on each other.

The outermost layer, therefore, having the outermost faces of the plurality of cells 10 arranged in this way, allows excellent support comfort for the user, without creating inconvenience or discontinuity.

Figures 3, 4:
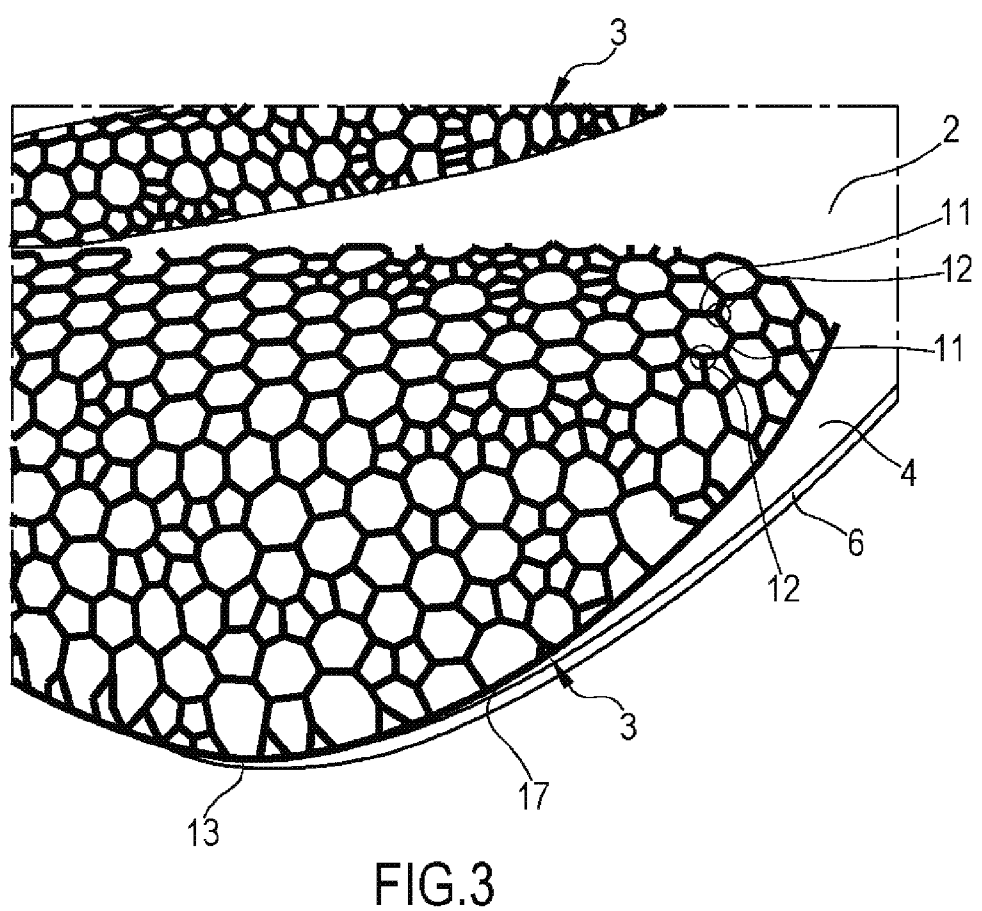
FIG. 3 is an enlarged detail of the saddle shown in FIGS. 1 and 2.
FIG. 4 is a detail view of a side portion of the saddle shown in the previous figures.

The faces of the various cells 10 comprise at least three substantially linear branches or sections 11 (or lateral with respect to the respective face), which join at at least three vertices 12 of the cell 10, as can be seen in the detail of FIG. 3.

As illustrated, the vertices 12 may not be distinguishable from the branches or sections 11; they are identifiable because they are the points of contact between one section 11 and the next, both of the same face of a cell, and of different faces of the same cell, and between adjacent cells.

Each cell 10 can have two faces substantially lying on parallel planes and at least two other faces arranged substantially perpendicular or orthogonal to the parallel faces or with a certain degree of draft. The parallel faces can be axially offset relative to each other or they can be arranged axially aligned.

Furthermore, the faces of the plurality of cells 10 of one layer can be positioned offset with respect to the faces of the plurality of faces 10 of an adjacent layer.

In one version of the invention, the space enclosed by the cells 10 and/or the faces of the cells 10 consists of an empty space. In this version, only the branches or sections 11 and the vertices 12 have a concrete structure, and/or are made of a given material, while the other areas of the cells 10 are empty, and/or not made of any given material, but formed from an opening. Therefore, the elastic and/or cushioning and/or bearing capacities of the second component or padding component 3 are mainly conferred by the branches or sections 11 and by the vertices 12, which therefore determine the aforementioned characteristics or properties.

As can be seen for example in FIG. 4, in at least one version of the present invention there is a substantially continuous terminal edge 13, which constitutes the outermost perimeter of the second component or padding component 3. This terminal edge 13 extends along the entire perimeter of the second component or padding component 3 in a substantially annular way.

Figure 1:
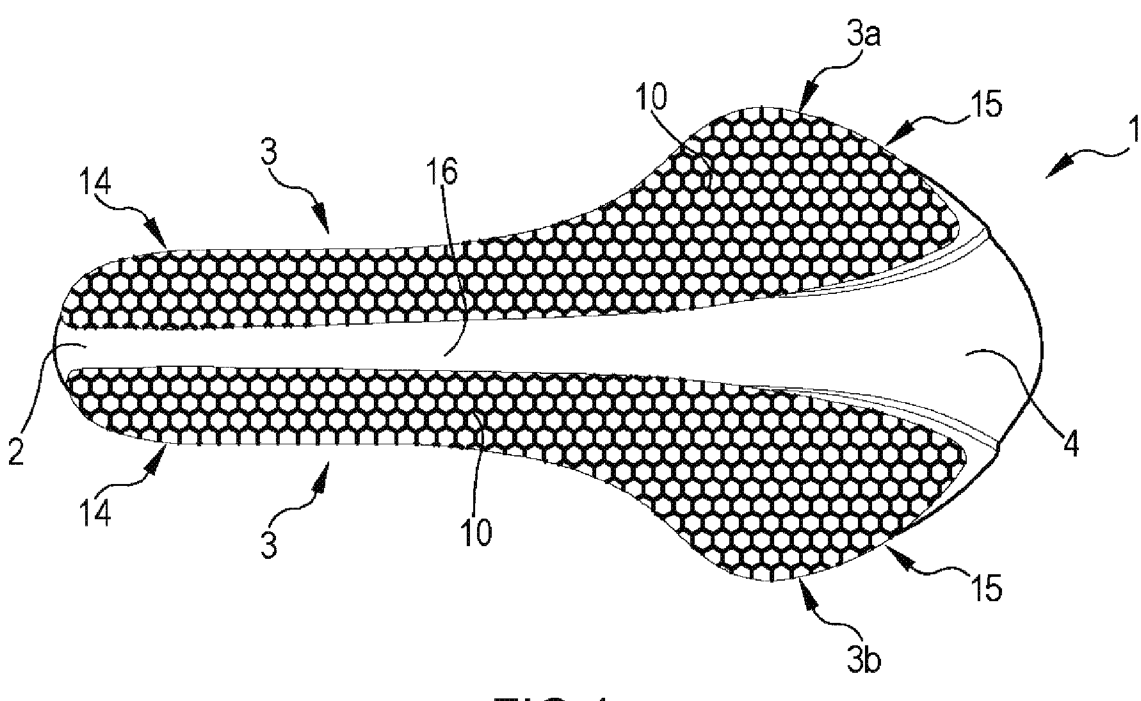
FIG. 1 is a top view of a bicycle saddle according to a version of the present invention.
Figure 2:
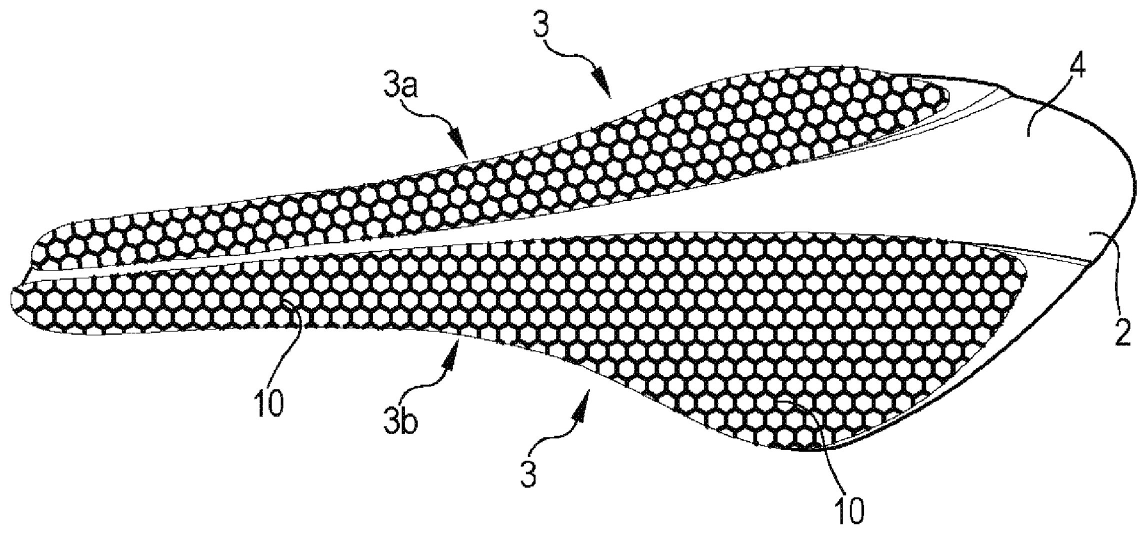
FIG. 2 is a side view slightly from above of the bicycle saddle of FIG. 1.

As can be seen, for example, in FIGS. 1 and 2, the second component or padding component 3 can be composed of at least two parts, a right side part 3*a* and a left side part 3*b*. Each right side part 3*a* and left side part 3*b* comprises a plurality of cells 10 as described above.

In the case of a bicycle saddle, each right side part 3*a* and left side part 3*b* has a first portion 14 having an elongated conformation towards the front F of the saddle and a second portion 15, having an enlarged conformation at the rear R of the saddle. The second portion 15 of the right side part 3*a* and left side part 3*b* is adapted to support the rear portion of the buttocks of a user.

As can be seen in the figures indicated, the right side part 3*a* is separated from the left side part 3*b* by a space 16.

The space 16 develops substantially longitudinally from the front F to the rear R of the saddle and, in at least one version thereof, has a substantially constant thickness for most of its development. At the rear R of the saddle, the thickness of the space 16 can widen (with respect to its thickness at the front F of the saddle).

In this version, the right side part 3*a* and left side part 3*b* are constrained and/or connected to the first component or support component 2, which also extends at the space 16. Therefore, the space 16 is closed at the bottom by the first component or support component 2. The latter also extends below the second component or padding component 3.

The right side part 3*a* and the left side part 3*b* may have different characteristics from each other, for example on the basis of the density of their various zones and/or on the level of lift and/or softness, for example in the case in which the user exerts a different pressure between right and left and/or is subject to an asymmetry of posture during pedalling.

Furthermore, an outer peripheral edge 17 of the first support component or component 2 can be positioned substantially correspondingly (for at least part of its extension) with respect to the terminal edge 13 of the second component or padding component 3.

In a version not shown in which the support element 1 is a bicycle saddle, the second component or padding component 3 can be unique, having a conformation substantially corresponding to that of the first component or support component 2. That is to say that the second component or padding component 3 can have an elongated or tapered conformation at the front F of the saddle while it can have a more enlarged conformation at the rear R of the saddle.

A peculiar feature of the present invention consists in the fact that the second component or padding component 3 can have cells 10 having different conformation and/or size and/or density and/or stiffness from cell to cell and/or from area to area of the second component or padding component 3.

For example, the second component or padding component 3 can be composed of cells 10, for example honeycomb cells, in which the mechanical response can be modulated through the size of the cell 10 and the thickness of the sides or branches that constitute it. A large cell "yields" more, as does a thinner branch. On the contrary, smaller cells or with thicker or thicker branches offer more resistance to crushing.

In the case of a saddle, it tends to include more yielding areas positioned at and supporting the soft tissues of the human body (for example at the tip and/or the front F of the saddle) and areas that are more sustained and/or more resistant and/or capable of providing greater support at the bones of the human body (for example the ischial bones and/or for example in correspondence with the rear R of the saddle and/or its widest part) or vice versa.

Furthermore, in at least one version of the invention, the padding component 3 comprises highly unstructured cells in those areas not designed to support the human body (for example the areas where one does not sit, for example the rear part of the saddle or tail) to lighten the structure.

Furthermore, in at least one version of the invention, the position of the different areas (in which, for example, a plurality of a certain cell rather than another is present) is determined by the pressure map generated by testing the user or the cyclist. A certain cell shape will be assigned to areas of higher pressure, as well as to areas with less pressure or no pressure. The way of identifying and interpreting the areas, as well as the dimensions of the cells are, for example, the result of the process and of the apparatus described in the present discussion. Therefore, the typology of the plurality of cells 10 (for example the shape and/or the size of the cells 10) and/or the typology of the branches or sections 11 (for example the number and/or the thickness and/or the length of the branches or sections 11) determines a different elasticity according to the zone or area of the saddle (or of the support element 1) being considered. In this way, the saddle or the support element 1 will have different zones capable of responding differently, as regards the levels of comfort and/or cushioning, from zone to zone on the basis of the real needs of the user.

The variability of elasticity and/or comfort and/or cushioning present from area to area of the second component or padding component 3 is given by the fact that the latter is made according to specific anatomical and/or weight and/or needs related to the user's pedalling style. In this way, the support element 1 will have a greater density at the user areas that require greater support. Conversely, the areas with a lower density will correspond to those areas of the support element 1 in which the user will need less support and/or greater comfort. The needs of the user can be detected, for example, by means of a pressure mapping method (of the user on a test or model or comparison support element and/or on a test or model or comparison second component or padding component).

For example, if the support element 1 is a bicycle saddle, the user is made to sit on a suitable test saddle (equipped with pressure sensors), which allows to detect the pressure exerted by him (at the lower back of the same) on the test saddle, in order to obtain a relative file.

The test saddle has an abutment surface substantially similar and/or corresponding to that of the saddle-shaped support element 1 which has to be obtained.

In the event that the support element is a grip 100, this will be the pressure exerted by the hand and/or the upper part of the torso and/or arm of the user, for example, on a test grip equipped with pressure sensors.

In the event that the support element is a shock-absorbing element 200, it will be a question of measuring the pressure of the user and at the same time the suspension/damping of the saddle (equipped with a test shock-absorbing element) for example on different types of terrain (for example simulated in the laboratory).

There is therefore a pressure detection device, possibly equipped with a series of sensors capable of detecting the pressure signals and/or the pressure exerted by the user on the test support element.

The detection device may also include a device for acquiring user (or cyclist) data such as personal data (age, sex, weight, height, build, posture, etc.) and/or data related to its modality/preference for performing the athletic or pedalling gesture, such as the pedalling style, the running style, the posture on the bicycle or vehicle, the type of performance you want to perform, etc.).

The detection device therefore includes both the test saddle (or the test grip or the test shock absorbing element), with which the user interacts in use, and the data acquisition device and the sensors system suitable for detecting the pressure exerted by the user on the test support element (the test saddle or the test grip or the test shock-absorbing element).

There is also a device for interpreting these entered data and/or detected signals, so that they can be analyzed in order to obtain, for example, a file in which they are possibly reported in conjunction with their specific interpretation and/or analyses.

From this mapping process, therefore, a file emerges that shows the pressure data found by the user, possibly compared and/or correlated to the other data of the user linked to his personal data and preferences for carrying out the sporting activity, in which such file can be collected, for example, in a database together with files of other users. The files and data present in the database can also be, if of interest and in at least one version of the invention, compared to each other in order to define categories of users that contain the files that present a similar or comparable response from different users and which define the type of user or cyclist to whom the user, from whom the first set of data was taken, appears to belong.

Figure 10:
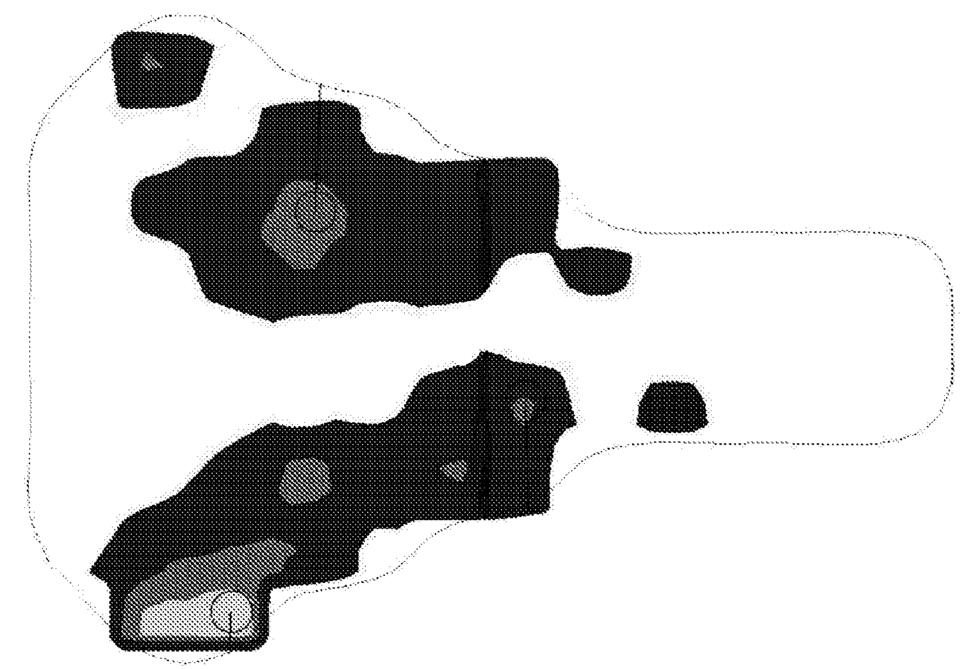
FIG. 10 illustrates an example of a pressure map that comes from a user.

The file, in at least one version of the present invention, can relate to a pressure map of the user. An example of this pressure map of the pressure exerted by a user on the test saddle is shown in FIG. 10.

Therefore, the detection device can comprise or be connected to a unit capable of processing the entered data and/or the detected signals in order to generate a first series of data relating to the anatomy and preferences of the user.

The method according to the present invention therefore comprises the possibility of detecting by means of the pressure detection means, the pressure exerted by the at least one anatomical part of the human body of a user on the test or test element, for example by means of a mapping step pressure.

As will be better understood in the following, the detection device can also be positioned in a remote position with respect to the site of realization of the support element 1, since the data found/entered there can be further analyzed and then sent by means of suitable support or online or uploaded to a platform such as a cloud, in order to be used for actual production. From the union of the previous parameters, possibly considering the category in which the user is classified, considering the possible pressure map as well as the modalities/preferences expressed by the user, a preferential match or combination that defines a certain form and certain desired characteristics for the support element 1 is obtained.

Therefore, the first series of data and/or any category attributed to the user are processed in such a way as to obtain a second series of data which defines the type and/or conformation of the support element according to the invention.

For example, the second data series comprises information relating to and/or defines the position, density and/or conformation of each cell 10 of the plurality of cells 10 and/or on the thickness of branches or sections 11 and vertices 12 of each cell 10 of the second component or padding component 3, 103, 203, and/or the type and/or conformation of the support element 1, 100, 200.

The above therefore represents a processing of the acquired data and their subsequent conversion into a file that can be read by a device suitable for making the support element 1

The detection device, therefore, can be connected for example via a telematic network such as the internet or a private network, etc., or via cable or via Wi-Fi. Bluetooth, and the like, via mobile or fixed devices. This telematic connection can also take place with the three-dimensional printing machinery with which the support element and/or at least the second component or padding component is actually made.

The first data series will then be transformed into a second data series and/or a special file, capable of being read by a three-dimensional printer.

Therefore, the above will essentially consist in:

provide a detection device capable of collecting user parameters and measurements useful for defining—at least—a support element and/or a second component or padding component 3 customized for the specific user, possibly compare the above data with an ad hoc database, such as a cloud storage system, for the definition of a specific meaning for the aforementioned data, provide software and/or an application, such as an app for a mobile device, and an interface system between the detection device, software and possibly the cloud, for the collection and processing of data, transform and/or translate the data into a file suitable to be used/read for the realization of the support element 1, such as for example for the 3D printing of the same, and/or supply the digital file or three-dimensional digital model to a 3D printing machine for the step of printing using a three-dimensional printing technique.

All this therefore refers to the acquisition and interpretation steps of the acquired data, as well as their processing and their conversion into a suitable resulting file, possibly by means of a specific algorithm.

In order to determine any aforementioned categories and/or match, in order for example to define an ideal profile for the user, it is possible to provide at least one of the following steps, in at least one version of the invention:

Evaluation of existing parameters both static (personal data of at least one cyclist, position, etc.) and dynamic (pedalling mode, type of performance, etc.), considering a sample that can include from 50 to 100 cyclists, for example, possibly divided based on gender.

Definition of at least one category of user by assigning a value to these parameters, Comparison of the individual parameters with the identified user categories, in order to identify which category best responds to the individual parameters.

Correlation of the identified user category with a determined conformation of a support element 1, such as a saddle, so as to produce a support element 1 having at least that defined conformation.

All this can be achieved by means of suitable algorithms and databases.

In an alternative version, it will be possible to have very precise data without going through categories and/or aggregated data: therefore precise data will be used to create the 3D file directly.

According to an embodiment example, from the study of the various pressure measurements of different users, or from the single user file, from the resulting match a series of signals are obtained which are translated—by means of specific algorithms—into data of a digital file or digital three-dimensional model of the support element 1, which has, as said, a second component or padding component 3 formed by a plurality of cells 10 whose conformations and dimensions can vary from cell to cell or from zone to zone to give a certain density on the based on the pressure exerted by the user on the support element and measured as indicated above.

In this way, the second component or padding component 3 will have the necessary support and the necessary comfort (and/or elasticity) according to the specific needs of the user.

In order to create this three-dimensional file or model, it may be useful to prepare a special interface for transferring data: from the measurement file to the conversion file that can be used for the subsequent 3D printing of the support element 1. It is then possible to move substantially, in at least one version of the invention, from a two-dimensional file (such as the pressure map can be) to a three-dimensional file, readable for example by a three-dimensional printer, which produces the plurality of cells 10. As mentioned, therefore, this three-dimensional file or model will then be used to provide for the formation of the support element 1 and/or its second component or padding component 3 by means of the three-dimensional printing technology.

The generated three-dimensional file, which includes the indication of the position, conformation and density and/or stiffness, etc. of the cells 10, starts from the base of a predefined 3D volume and which identifies the final shape or conformation of the saddle and/or of the support element 1 and/or its second component or padding component 3. Basically, we go to “populate” or fill the predefined 3D volume with 3D cells. In at least one version, therefore, from the two-dimensional file a three-dimensional is not automatically generated, but from the two-dimensional file it is possible to read the data represented by the pressure areas through values, colours or greyscale, data which in turn correspond to a form of predefined cell that will be repeated within the predefined 3D volume with different density and thickness.

A certain type of cell will correspond to a certain colour or pressure value 10.

This file will undergo another manufacturing process to make it a 3D printing executable code (slicing, as indicated below in more detail).

Figure 9:
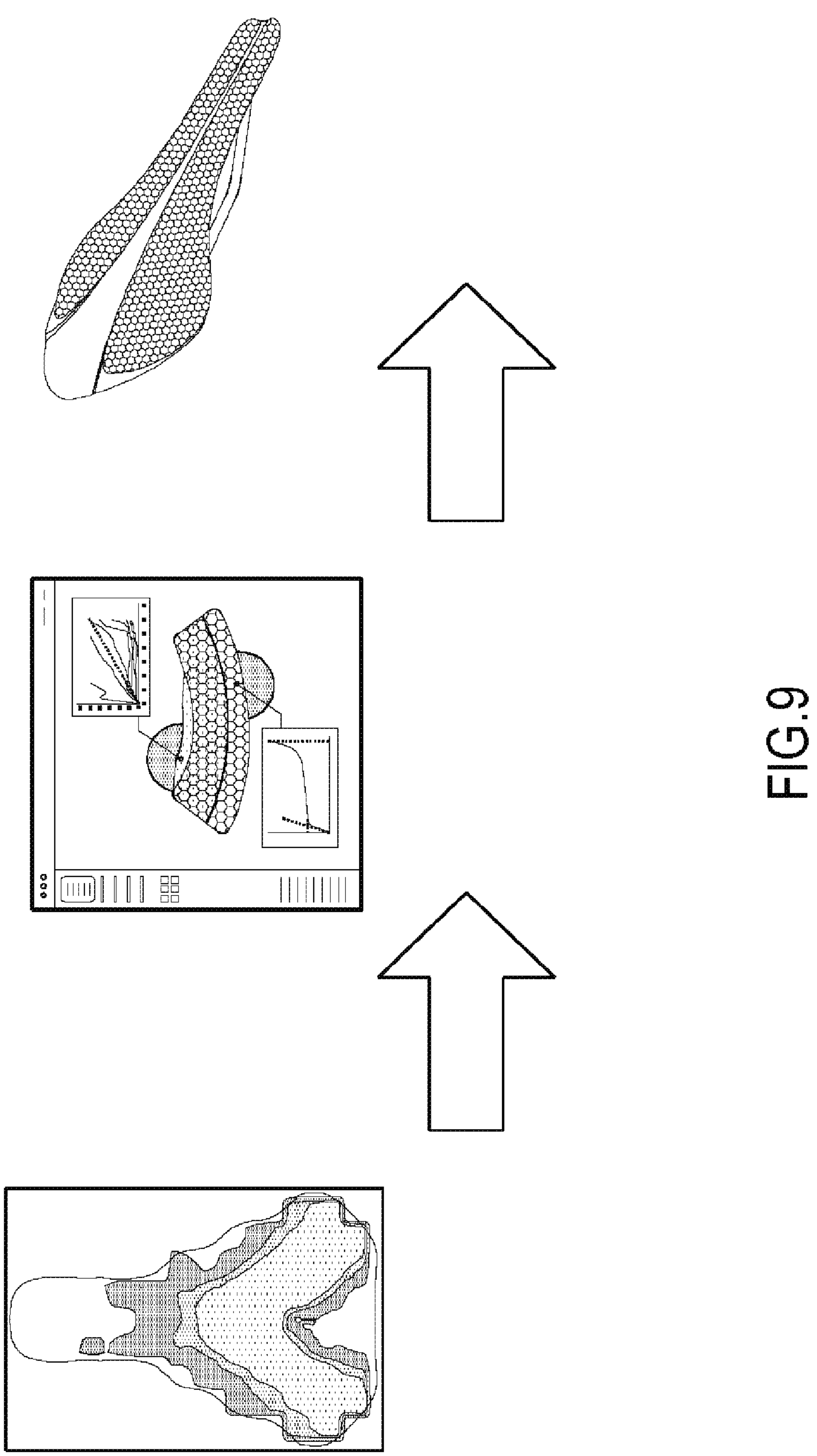

An example of this procedure is illustrated for example in FIG. 9.

In particular, the left figure shows an example of a user’s pressure mapping on a test saddle, the central figure shows an example of the three-dimensional file or model which—from the type of pressure mapping—determines a certain conformation of the plurality of cells 10 of the second component or padding component 3, and finally in the figure on the right the finished object printed by means of three-dimensional printing technology is illustrated. According to a further version, when the pressure is detected, a pressure map is generated for a user, the output of which is a rectangular photo or image with given dimensions (for example shown in FIG. 10). The dimensions are extremely important to allow automatic positioning within the app, as better indicated below. This passage is for example carried out by means for processing and/or translating a plurality of pressure signals into a first series of data defining a pressure map.

For example, this photo or image or this pressure map shows at least for each point of contact and/or contact area between the user and the test element a certain pressure value (which corresponds to the one actually detected). This occurs along the entire contact surface between the user and the test element and, possibly, also in the areas close to the contact surface.

This photo or image is imported into an app that automatically positions it on a Cartesian work surface, in which there is also a representation of the volume that constitutes the padding component 3 to be printed and/or is determined by it.

Figure 11:
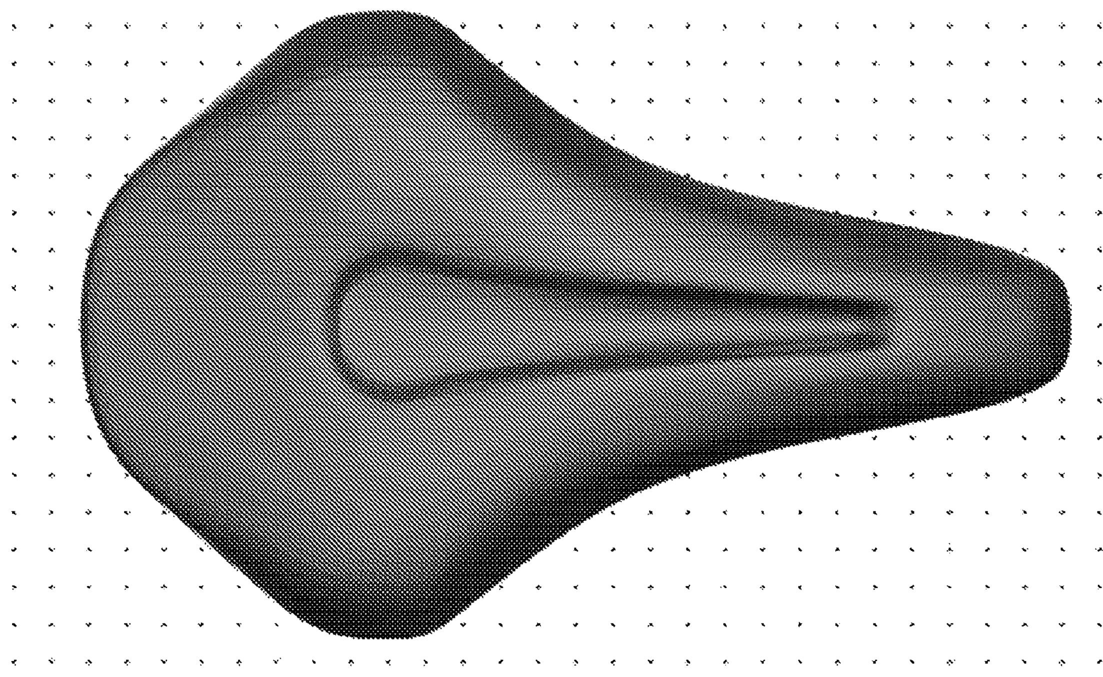
FIG. 11 illustrates an example of the volume of a 3D padding within an app.
Figure 12:
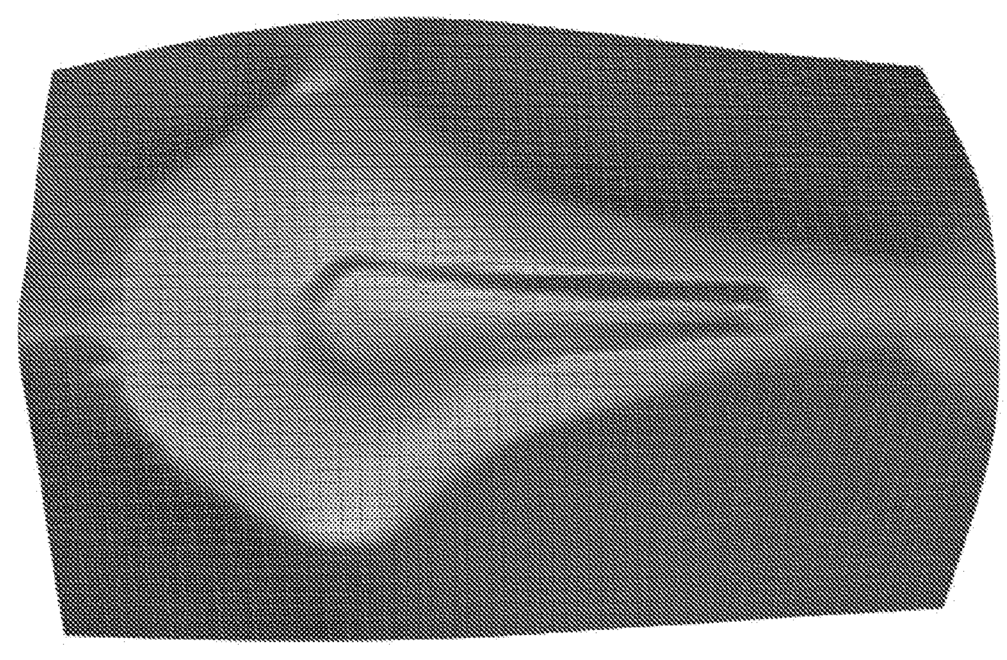
FIG. 12 illustrates an example of a UV map within the app, generated once and for each model.

An example of a 3D volume of the padding component 3 as shown in the dedicated app is represented for example in FIG. 11. The volume of the padding component 3 can vary according to the type of use to be made. For example, it can be a more contained and/or compact volume, if the type of saddle is to be used in professional situations, and/or competitions, etc. while it can be a greater volume, with greater shock absorbing area, if the use of the saddle is mainly city and/or amateur type. This selection will take place, in at least one version of the invention, by defining whether the user belongs to a certain category of use and/or pedalling.

Figure 13:
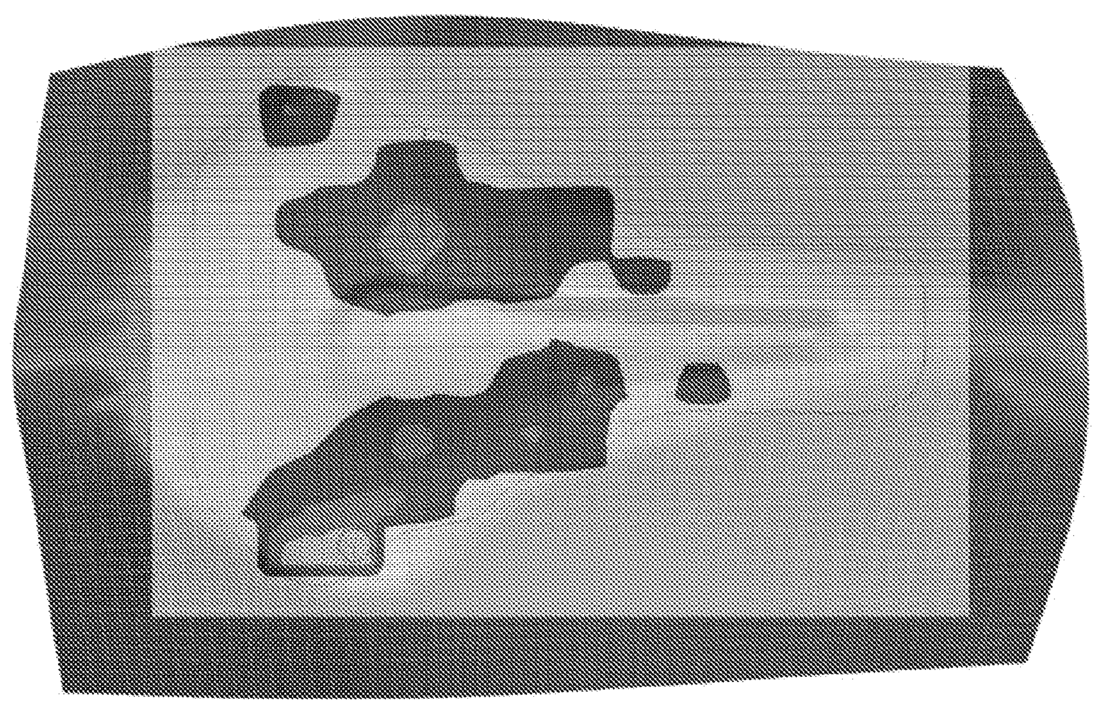
FIG. 13 illustrates the pressure map of FIG. 10, which follows the at least one curvature of the padding based on the UV map of the model of FIG. 12, conforming to the at least one curvature, automatically through at least one algorithm.

The volume to be printed is mapped (only once for each model in the design phase) through a UV map (as shown in FIG. 13).

The 3D volume of the padding component 3 to be printed has at least one curvature, corresponding in use at least to part of the external surface 8 of the padding component 3 or at least to the whole external surface 8 and/or to the curvatures necessary to ensure aerodynamics and/or ergonomics and/or comfort and/or the correct anatomy of the padding component 3 itself.

Figure 14:
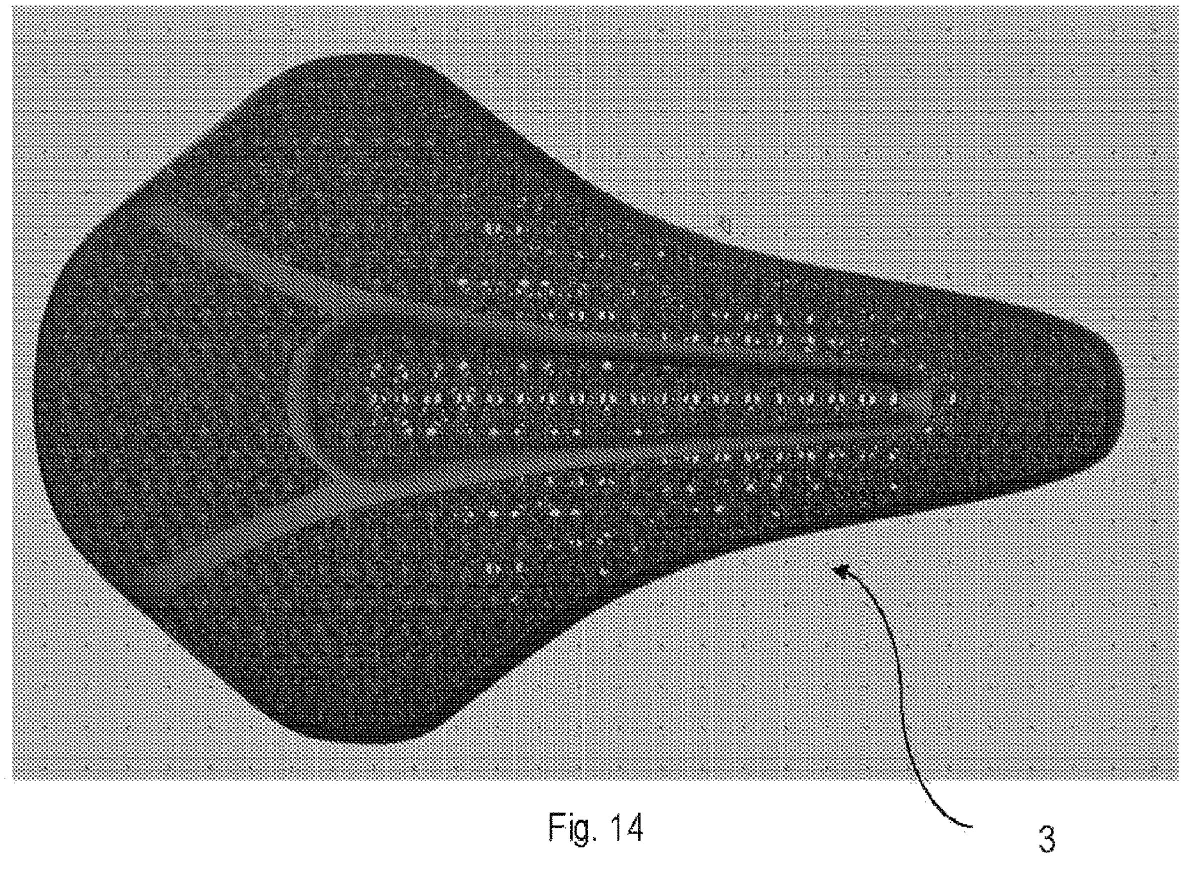
FIG. 14 illustrates the printing padding, which is generated by an algorithm which determines the various cells at least in size and density.

The pressure map is hooked onto this UV-map and the latter assumes a conformation corresponding to that of the at least one curvature of the 3D volume (or for example a double curvature, i.e. a conformation that presents a shape given by the intersection of at least one curvature of the 3D volume both on a ZX plane and on a ZY plane, which correspond to the Cartesian and/or orthogonal planes that intersect with the figure and/or with the volume of the support element. For example, in at least in a version of the invention, an organic shape is obtained which does not have rectilinear sections on the various planes indicated) in order to better follow the shape of the padding component 3 to be printed. Through at least one algorithm in the dedicated app, the various shades of grey—or from white to black—of the pressure map, which determine the pressure variations exerted by the user on the test saddle, are read automatically and based on the depth of the black and/or the intensity of the grey scale, the algorithm assigns specific parameters to each single cell determined in the 3D volume and/or in the UV-map, adjusting its density and size, for example by means of specific standards established by the manufacturer (the printed padding component is visible for example in FIG. 14). This step is for example carried out by means of transforming the first data series defining the pressure map into a second data series to obtain a three-dimensional digital file or digital model of the padding component 3, with particular reference to the density, conformation and/or position of its cells 10 and/or the thickness of the branches or sections 11 of the cells 10.

The logic foresees that on the points with greater pressure (black colour) there is possibly a lower density of cells and/or a smaller diameter of the branches or sections 11 of each cell 10, so as to have less resistance on the part of the padding component and therefore a better comfort for the user, with relief for the pressure exerted.

On the contrary, in the areas where the pressure is lower (for example light grey colours), the logic of the algorithm is exactly the opposite, resulting in a greater density of cells and/or a greater diameter of the branches or sections 11 of each cell 10, in order to guarantee greater resistance and support from the padding component.

Where, on the other hand, there is no pressure detected (white colour), the algorithm assigns parameters to each cell 10, for example a deconstructed or emptied cell, to obtain a reduction in the weight of the padding component 3.

Naturally, intermediate shades of grey will provide density and/or diameter of the branches or sections 11 intermediate with respect to those indicated above.

In this way, it is possible to obtain a support element 1 customized to measure according to the real needs, including anatomical ones, of the user.

For example, in the final support element, obtained by 3D printing, each cell 10 will be positioned and/or shaped and/or made on the basis of specific pressure data, and/or on the basis of the category to which it belongs or the needs and tastes of the user, in order to obtain a complete customization of the support element itself or at least of its second component or padding component.

In this case, as mentioned, in at least one version of the invention, localization can also take place, again by defining the possible category to which the user belongs and/or his specific needs and/or by analysing the conformation of the support element 1 resulting from the analysis of the aforementioned data, of the various areas with different characteristics as mentioned above.

According to a version of the invention, the first component or support component 2 can also be made by means of a three-dimensional printing technique.

In this case, the first component or support component 2 does not have a plurality of cells since it must perform its support function and the presence of the voids inside the cells could compromise this function.

Although the first component or support component 2 cannot be populated by cells, in at least one version of the invention it can be emptied on the basis of tension areas obtained from the application of loads that simulate their use, these maps can be defined using finite element simulation methods and the component topology can be hollowed out to eliminate non-stressed areas. From this type of approach, complex shapes can be generated that only additive printing can create/produce.

Therefore, the first component or support component 2 is molded three-dimensionally in order to obtain a substantially continuous and/or solid structure, capable of having the necessary mechanical characteristics.

Optionally, this printing step also involves the bond and/or adhesion of the first component or support component 2 with the second component or padding component 3.

The material which constitutes the second component or padding component 3 and/or the branches or sections 11 and the vertices 12 of the cells 10 is a plastic material and/or a polymeric material, such as for example a thermosetting material or a thermoplastic material. Such plastic and/or polymeric material can comprise, for example, at least one of the following materials or resins: a polyurethane (PU), a thermoplastic polyurethane (TPU), a thermoplastic resin, at least one component of the family of thermoplastics, preferably TPU, others polymers, etc.

The plastic and/or polymeric material can also comprise, in at least one version of the present invention, reinforcing fibers such as for example carbon fibers, glass fibers. Kevlar, etc. According to a version of the invention, the three-dimensional printing technique of the DLP or DLS type uses a liquid starting material, whereby the printing material will not comprise reinforcing fibers. This is especially true for the second component or padding component 3.

For the realization of the first component or support component 2, on the other hand, the three-dimensional printing techniques can be different from those of printing the second component or padding component 3, for example FDM or MJF or SLS or other, and in this case it is possible to use materials loaded with these reinforcing fibers.

The use of the aforementioned technology for the present invention therefore allows to review the production processes since, unlike the normal padding components made for example of polyurethane, which must be foamed, the usual foaming molds are no longer necessary, the carousel on which the molds and the relative foaming machines are installed. The 3D printing technique applied to the present invention also makes it possible to reduce the complexity of the management of the chemistry currently required to produce polyurethane padding, with a consequent reduction also in terms of emissions and disposal of waste due to the polyurethane foaming phase.

In the version in which the first component or support component 2 is also made by 3D printing, the material with which it is made will be a thermosetting material, or a thermoplastic material, or a material comprising fillers or reinforcing fibers, equal to or different from that which constitutes the first component or padding component 3.

In this case, also the first component or support component 2 is customized and thus responds to the real needs, including anatomical ones, of the user.

If, on the other hand, the first component or support component 2 is not made by 3D printing but by traditional techniques, it can be made for example in carbon and/or in a thermoplastic material and/or in a composite material.

The fork component, in the version in which the support element 1 is for example a bicycle saddle, which can connect the second component or support component 2 to the frame of the bicycle itself, can be made for example of steel and/or carbon, and/or in a new type of material.

The technology of the present invention also allows to remove the minimum production orders; moreover, any modification or design change required for the support element 1 only results in an update of the related three-dimensional file.

The support element 1 is therefore an element completely adaptable to the various needs of the user.

In the version illustrated for example in FIGS. 5 to 7, the support element 1 has the shape of a handlebar grip 100. Elements identical to those previously described will be indicated with the same reference numbers, increased by 100 units.

The handlebar grip 100 therefore comprises a first component or support component 102 and a second component or padding component 103.

The first component or support component 102 substantially has the same characteristics already described, which will therefore not be repeated. At the configuration level, the first component or support component 102 has a substantially tubular shape, with a substantially circular cross-section, provided with a first surface 104, with a second surface 105 and with a thickness 106.

The first surface 104 is able to come into contact and/or to be positioned and/or constrained to one end of a handlebar of a bicycle or similar vehicle while the second surface 105 is able to come into contact with the second component or padding component 103.

The first component or support component 102 also has a proximal end 102*a* and a distal end 102*b*, opposite the proximal end 102*a* and adapted in use to be positioned more externally with respect to the handlebar of the bicycle or vehicle.

At the proximal end 102*a* there may be means for fastening to the handlebar of the bicycle or vehicle, of a known type and therefore not further described.

The second component or padding component 103 also has a tubular conformation with a substantially circular and/or annular cross-section, and is equipped with an internal surface 107 capable of coming into contact and/or binding with the first component or support component 102, and an external surface 108, opposite the internal surface 107.

The external surface 108 is adapted in use, in at least one version of the invention, to be placed in contact, for example, with the hand of a user or to be covered by a covering element as described above, if present.

The second component or padding component 103 also has a thickness 109 corresponding to the distance between the internal surface 107 and the external 108.

Also in this case, the padding component is composed of a plurality of cells 10, having the properties described above.

In at least one version of the present invention, the second component or padding component 103 can cover the distal end 102*b* by means of a substantially circular portion thereof.

In an alternative version, instead of the substantially circular portion, a suitable cap for covering and/or closing the distal end 102*b*, for example of a known type, can be provided. In FIG. 8, the support element 1 has the conformation of a shock-absorbing element 200 for a saddle or seat for the human body. The shock-absorbing element 200 can be defined as a suspension element for a saddle or seat for the human body.

Elements identical to those previously described will be indicated with the same reference numbers, increased by 100 units.

The shock-absorbing element 200 comprises a first component or support component 202 and a second component 203.

The first component or support component 202 substantially has the same characteristics already described, which will therefore not be repeated. At the configuration level, the first component or support component 202 comprises a first discoidal base 202*a* and a second annular base 202*b*, connected by a substantially tubular wall 202*c*. The discoidal base 202*a* is able to come into contact and/or to be associated and/or constrained to the second component 203. The annular base 202*b*, on the other hand, is opposite to the discoidal base 202*a*. There is also a through opening 202*d*, having a substantially circular section, the extension of which involves at least the annular base 202*b* but can also involve the substantially tubular wall 202*c* up to the discoidal base 202*a*.

The wall 202*c* constitutes a recessed area with respect to the annular base 202*b* and/or the discoidal base 202*a*, suitable in use to house, for example, the rear portion (possibly having a hooked or substantially circular shape) of a fork (not shown) of a bicycle saddle.

The second component 203 constitutes a shock-absorbing or suspension element for the bicycle saddle or the seat and is composed of a plurality of cells 10 having the characteristics described above.

The second component 203 has a substantially hemisphere conformation, provided with a hemispherical cap 203*a* and a flat base 203*b*.

The flat base 203*b* is adapted to come into contact and/or to bond with the discoidal base 202*a* of the first component or support component 202.

Also in this case it is possible that there is a perimeter edge 13 which is constrained to an outer peripheral edge 17 of the first component 202 and/or of the discoidal base 202*a*.

At the apical region of the hemispherical cap 203*a*, the support element 200 is connected to the saddle or seat by means of connection means of the per se known type.

In this embodiment, the discoidal base 202*a* has a second surface 205, suitable for binding to the second component 203, and a first surface 204 (for example at the annular base 202*b*), as well as a thickness 206. The thickness 206 is given by the sum of the thickness of the discoidal base 202*a*, of the annular base 202*c* and the height of the wall 202*c*. The opening 202*d* can have an extension at least equal to or less than the thickness dimension 206.

The second component 203 also has an internal surface 207 suitable for coming into contact and/or binding with the first component or support component 202, and an external surface 208, opposite the internal surface 207.

The external surface 208 can be covered with a covering element as described above, if present.

The second component 203 of the shock-absorbing element 200 also has a thickness 209 corresponding to the distance between the internal surface 207 and the external surface 208. In general, considering the various embodiments described above, the plurality of cells 10 forms a sort of "latex" or cross-linked or open cell structure.

In one version of the invention, the second component or padding component can be molded directly onto the first component or support component. Otherwise, it can be bound on the same by means of special gluing means.

The density variation or transaction of the at least one second component or padding component can occur in discontinuous areas or continuously along the entire extension of the support element 1 and/or of the second component or padding component.

In the latter case, the realization of areas or zones having properties or densities different from each other will be obtained without solution of continuity, that is to say in a gradual and continuous way for the whole extension of the second component or padding component. This solution is not achievable with traditional manufacturing methods, for example of the padding element, such as in this case the foaming technique and/or known molding equipment.

The three-dimensional printing technology can be the one known by the trade name "Digital Light Synthesis" (or DLS), which allows to obtain the printed product starting from a three-dimensional digital file or digital model and which is turned out to be a very quick technique. Other three-dimensional printing techniques can also be used, as mentioned above.

In the version in which the second component or padding component is molded directly onto the first component or support component, it is possible for the second component or padding component to be molded as described above, then placed in position on the first component or support component and it is bound to the latter when subjected to a heat source for its hardening.

Furthermore or alternatively, it is possible to carry out an initial polymerization with UV and then apply heat to accelerate the internal crosslinking, for example by means of a suitable oven.

In this way, a bond is also created with the lattices of the polymer of the first component or support component, determining its adhesion or a stable and lasting bond.

This phase can be facilitated by using a suitable primer positioned and/or spread on the first component or support component before placing the second component or padding component on it.

Furthermore, the covering material or the covering element could be treated in the same way to fix the parts together and/or to fix this covering element to the second component and/or to the first component, exploiting the polymerization of the printed material in 3D to also hook onto a possible covering or covering element, which is for example made of a synthetic or other material, but suitably treated to be chemically compatible for application on the second component and/or on the first component.

In any case, after the realization of at least the second component or padding component by means of the three-dimensional printing technique, the support element is assembled and is ready for sale.

The object of the present invention is also an apparatus for the realization of a support element 1 for the human body, such as for example a bicycle saddle or of a vehicle in general, a grip 100 for a handlebar of a bicycle or of a vehicle in general, a shock-absorbing or suspension element 200 for a saddle or seat for the human body.

The present invention could also relate to an apparatus for making an insert or element for absorbing shocks or impacts for a helmet, for example for cycling, a shock-absorbing insert placed for example between the support component and the padding component of a bicycle saddle or on top of the padding component, or on top of any covering element that covers the padding component, a pad-insert for a cycling shorts, a sole or inner sole of a sports and/or cycling shoe.

The support element 1 comprises a first component or support component 2, 102, 202 and a second component or padding component 3, 103, 203 which is constrained to the first component or support component 2, 102, 202 and in which the second component or padding component 3, 103, 203 comprises a honeycomb structure comprising a plurality of cells 10. This apparatus comprises means for detecting the pressure exerted by at least one anatomical part of the human body of a user on a test element, which can be used to generate a plurality of output signals. In particular, the detection means can comprise, in at least one variant of the invention, a plurality of pressure sensors positioned on the test element.

Means are then provided for processing and/or translating the plurality of signals into a first series of data defining a pressure map associated with the pressure exerted by at least one anatomical part of the user's human body on the test element. In particular, the processing and/or translation means can comprise, in at least one variant of the invention, a first computerized logic unit with at least a first computer program or software configured to process and/or translate the plurality of output signals obtained by the sensing means (for example a series of pressure values measured by the sensing means or pressure sensors) so as to generate the first series of data (for example a series of colour shades, for example white and/or grey to black, corresponding to growing pressure values, for example wherein the white colour corresponds to pressure equal to zero, the black colour corresponds to the maximum detected pressure and the intermediate pressures correspond to grey shades more dark as higher are the measured pressure values).

The apparatus then provides means for transforming the first data series into a second data series (for example corresponding to position, density, configuration, thickness and/or length of the sections or branches 11, thickness and/or size of the vertices 12) to obtain a three-dimensional digital file or digital model of said support element 1, 100, 200.

The second series of data, according to at least one version of the present invention, is therefore represented in output by a 3D printing file that can be automatically loaded into the printer or 3D printing machinery for the realization of the support element.

To obtain this output, the values of the first data series (pressure map) are used, which are processed by an algorithm to interpret the various colour shades, for example grey, of the pressure map and to create—from a solid volume composed of surfaces and/or at least one curvature—a volume populated by a plurality of cells 10, and/or by an alveolar and/or lattice structure which, based on the pressure map and the algorithm, defines the cell density 10, the thickness of the sections or branches 11 and also the shape of the cell 10 itself.

In particular, the transformation means can comprise, in at least one variant of the invention, a second computerized logic unit with at least a second computer program or software configured to translate the first data series into the second data series. Said second computer program or software can advantageously comprise at least one data segmentation or data slicing algorithm for transforming the first data series into the second data series. This data segmentation or data slicing algorithm makes it possible to obtain a second series of data that is more easily viewable and interpretable than the first series of data.

Finally, means are provided for the three-dimensional printing of the support element 1, 100, 200 on the basis of information present in the three-dimensional digital file or digital model. In particular, the means for three-dimensional printing can preferably comprise, in at least one variant of the invention, a three-dimensional printing, for example of the "Digital Light Synthesis" or DLS type, or of the DLP or "Digital Light type Processing" type or of the type FDM or "Fused Deposition Modeling" type or MJF or "Multi Jet fusion" type or SLS or "Selective Laser Sintering" type.

The apparatus, in at least one variant of the invention, can then comprise acquisition means designed to acquire or store data of other users: such data can be personal data such as, for example, age, sex, weight, height, build, posture, etc., and/or data related to the mode/preference for performing the athletic or pedalling gesture, such as, for example, the pedalling style, the running style, the posture on the bicycle or vehicle, the type of performance wants to perform, etc.

Furthermore, in at least one variant of the invention, the apparatus can comprise means for comparing the first series of data with the data of other users contained or stored in an ad hoc database, such as for example a cloud storage system, so as to assign a certain meaning to the first data series, where the meaning may possibly include the definition of a category for the user, where the category includes data and/or files of other users that present a similar or analogous response to the first series of data. In particular, the comparing means, if present, can advantageously comprise at least a third computer program or software, for example a coupling or "matching" algorithm, stored in the first or second computerized logic unit. Such third computer program or software is configured to associate or match the first data series with data and/or files of other users which have a similar or comparable reply to the first series of data.

For example, in this way a specific 3D model or volume of a padding component can be identified, considered more suitable for a particular category of users in which—through the specific data collected—also the user in question falls.

It has thus been seen how the present invention achieves the intended aims.

The invention thus conceived is susceptible of numerous modifications and variations, all of which are within the scope of the inventive concept.

The features presented for one version or embodiment can be combined with the features of another version or embodiment, without departing from the scope of the present invention. Furthermore, all the details can be replaced by other technically equivalent elements. In practice, the materials used, as well as the contingent shapes and dimensions, may be any according to requirements without thereby abandoning the scope of the protection of the following claims.

The invention claimed is:

1. A method for making a support element for a human body, including a saddle for a bicycle or a vehicle, a grip for a handlebar of a bicycle or a vehicle, a shock-absorbing or suspension element for a saddle or seat for the human body, wherein said support element comprises a first component or support component and a second component or padding component which is constrained to said first component or support component, wherein said second component or padding component comprises a honeycombed structure comprising a plurality of cells, each cell comprising branches or sections and vertices, comprising the following steps:

providing means for detecting the pressure exerted by at least one anatomical part of the human body of a user on a test element, said detection means being designed to generate a plurality of output signals, detecting by means of said pressure detection means, a pressure exerted by said at least one anatomical part of the human body of a user on said test element, by means of a pressure mapping step, obtaining said plurality of output signals in the form of pressure values from said detecting step, providing means for processing and/or translating said plurality of output signals into a first data series defining a pressure map associated with the pressure exerted by said at least one anatomical part of the human body of said user on said test element, wherein said first data series comprises for example a series of colour shades, for example from white and/or grey to black, corresponding to increasing pressure values;

processing and/or translating said plurality of output signals into said first data series, providing means for transforming said first data series into a second data series to obtain a three-dimensional digital file of said second component or padding component;

transforming said first data series into said second data series, for example wherein said second data series comprises information relating to and/or defines a position, density and/or conformation of each cell of said plurality of cells and/or a thickness of said branches or sections and vertices of each cell of said second component or padding component, and/or the type and/or the conformation of said support element and obtain said three-dimensional digital file of said second component or padding component, providing means for three-dimensional printing of said second component or padding component, and printing said second component or padding component comprising said honeycombed structure by means of a three-dimensional printing technique on the basis of information present in said three-dimensional digital file, wherein said printing step comprises a step of providing and printing a material which constitutes said second component or padding component and said branches or sections and vertices of said plurality of cells, wherein said material is a plastic or polymeric material and wherein said step of printing by means of a three-dimensional printing technique comprises printing each cell of said plurality of cells having a polyhedral or parallelogram shape, comparing said first data series with the data of other users contained in an ad hoc database, such as for example a cloud storage system, in order to attribute a certain meaning to said first data series, wherein said meaning includes the definition of a category for the user, wherein said category includes data and/or files of other users that present a similar or analogous response to said first data series.

2. The method according to claim 1, comprising the steps of:

providing said first component or support component, putting into contact and constraining or causing adhesion of said first component or support component and said second component or padding component.

3. The method according to claim 1, wherein said detecting step comprises:

detecting, by means of said pressure mapping step and by means of said detection means, the pressure exerted by a user who is seated on a test saddle equipped with pressure sensors and a comparing seating surface corresponding to said second component or padding component, or detecting, by means of said pressure mapping step and by means of said detection means, the pressure exerted by a hand or by an upper part of the torso or arm of a user resting on a handlebar of a bicycle or of a vehicle equipped with a test grip equipped with pressure sensors and with a comparing surface corresponding to said second component or padding component of said grip, or detecting, by means of said pressure mapping step and by means of said detection means, the pressure exerted by a user who is seated on a test saddle and the suspension and/or cushioning exerted by a test shock-absorbing element equipped with pressure sensors and corresponding to said shock-absorbing element.

4. The method according to claim 1, comprising a step of providing a device for acquiring user data such as personal data, age, sex, weight, height, build, posture, and/or data related to the mode/preference for performing the athletic or pedalling gesture, such as the pedalling style, the running style, the posture on the bicycle or vehicle, the type of performance to be carried out, and a step of entering said data into said acquisition device in order to translate said entered data into said first data series as well.

5. The method according to claim 1, comprising at least one of the following steps:

providing a software and/or an application, including an app for a mobile device, and an interface system between the detection device, software and the cloud, for the collection and processing of data, processing said first data series and said category attributed to the user in order to obtain said second data series, providing said three-dimensional digital file to a 3D printing machine for said step of printing by means of a three-dimensional printing technique.

6. The method according to claim 1, wherein said plastic or polymeric material is a thermosetting or thermoplastic material, or a material comprising at least one of a polyurethane (PU), a thermoplastic polyurethane (TPU), a thermoplastic resin, at least one component of the thermoplastic family, other polymers, and/or wherein said method comprises a step of providing and molding a material which constitutes said first component or support component, wherein said material is a thermosetting material or a thermoplastic material or a loaded and/or including reinforcing particles material.

7. The method according to claim 1, wherein said step of printing by means of a three-dimensional printing technique comprises a three-dimensional printing step of the "Digital Light Synthesis" or DLS type, or of the DLP or "Digital Light Processing" type or of the FDM or "Fused Deposition Modeling" type or MJF or "Multi Jet fusion" type or SLS or "Selective Laser Sintering" type.

8. The method according to claim 1, wherein said step of printing by means of a three-dimensional printing technique comprises printing each cell of said plurality of cells comprising at least one face having a substantially parallelepiped or polygonal conformation, including a triangle, square or rectangle, hexagon, pentagon, octagon, or printing for said at least one face or for said at least one cell at least three of said branches or sections substantially linear, which join together at at least three of said vertices.

9. The method according to claim 1, wherein said step of printing by means of a three-dimensional printing technique comprises printing said honeycombed structure comprising a plurality of cells with different conformation and/or size and/or density and/or stiffness cell to cell or area to area of said second component or padding component, based on the anatomical and/or weight and/or desired needs of the user or printing external faces of said plurality of cells in a substantially coplanar manner with respect to each other the other so as to constitute an external surface of said second component or padding component.

10. The method according to claim 1, comprising a step of providing a covering element, comprising a film or thin layer consisting of a plastic material or a natural material, and placing said covering element over or to cover said second component or padding component.

11. The method according to claim 1, wherein said printing step comprises printing, for said second component or padding component, a substantially continuous terminal edge which develops in a substantially annular way, adapted to constitute the outermost perimeter of said second component or padding component.

12. The method according to claim 1, comprising a step of providing said second component or padding component in at least two parts, and/or in the case where said support element is a bicycle or vehicle saddle, in a right side part and a left side part equipped with a first portion having an elongated conformation towards a front (F) of the saddle and a second portion, having an enlarged conformation at a rear (R) of the saddle or wherein said right side part is separated from said left side part by a space which develops substantially longitudinally from the front (F) to the rear (R) of the saddle.

13. A support element for the human body, including a saddle for a bicycle or a vehicle, a grip for a handlebar of a bicycle or a vehicle, a shock-absorbing or suspension element for a saddle or seat for the human body, wherein said support element comprises a first component or support component and a second component or padding component which is constrained to said first component or support component, obtainable with the method according to claim 1, wherein said second component or padding component comprises a honeycombed structure comprising a plurality of cells comprising branches or sections and vertices and is made by three-dimensional printing, wherein each cell of said plurality of cells has a polyhedral or parallelogram shape, and wherein said second component or padding component and said branches or sections and vertices of said plurality of cells are made of a plastic or polymeric material.

14. The support element according to claim 13, wherein said first component or support component is made by means of three-dimensional printing or wherein said second component or padding component constrained to said first component or support component is fixed or adhered to the latter.

15. The support element according to claim 13, wherein each cell of said plurality of cells includes at least one face having a substantially parallelepiped or polygonal conformation, for example a triangle, square or rectangle, hexagon, pentagon, octagon.

16. The support element according to claim 13, wherein said honeycombed structure comprising a plurality of cells has different conformation and/or size and/or density and/or stiffness from cell to cell or from area to area of said second component or padding component, based on the anatomical and/or weight and/or desired needs of the user.

17. The support element according to claim 13, wherein said first component or support component comprises a first surface, a second surface opposite said first surface and a thickness, given by the distance between the first surface and the second surface while said second component or padding component comprises an internal surface capable of coming into contact and being constrained to said first surface of said first component or support component, an external surface opposite to said internal surface and a thickness given by distance between internal surface and external surface, wherein said second component or padding component constitutes an elastic and/or shock-absorbing and/or comfort portion of said support element while said first component or support component constitutes a rigid position of said support element to support the weight of the user and to guarantee a rigid structure to said support element.

18. The support element according to claim 13, wherein said external faces of said plurality of cells are substantially coplanar with each other so as to constitute said external surface of said second component or padding component or wherein said at least one face or said at least one cell comprises at least three of said branches or sections substantially linear, which join together at at least three of said vertices.

19. The support element according to claim 13, wherein said support element comprises a covering element, for example in the form of a film or thin layer made of a plastic material or a natural material, placed over or to cover said second component or padding component and/or wherein said second component or padding component comprises a substantially continuous terminal edge, which constitutes the outermost perimeter of said second component or padding component and extends in a substantially annular manner.

20. The support element according to claim 13, wherein said second component or padding component is composed of at least two parts, and in the case wherein said element support is a bicycle or vehicle saddle, said second component or padding component comprises a right side part and a left side part equipped with a first portion having an elongated conformation towards a front (F) of the saddle and a second portion, having an enlarged conformation at a rear (R) of the saddle or wherein said right side part is separated from said left side part by a space which develops substantially longitudinally from the front (F) to the rear (R) of the saddle.

21. The support element according to claim 13, wherein said support element is in the form of a grip for a handlebar, wherein said first component or support component has a substantially tubular shape, with a substantially circular cross-section, wherein said first surface is adapted to come into contact and to be positioned or constrained to one end of a handlebar of a bicycle or of a vehicle while said second surface is adapted to come into contact with said second component or padding component, wherein said second component or padding component has a tubular conformation with substantially circular or annular cross-section and is equipped with said internal surface able to come into contact and/or to constrain to said first component or support component and said external surface is able in use to be placed in contact for example with a hand of a user or to be covered by a covering element.

22. The support element according to claim 13, wherein said support element is in the form of a shock-absorbing element for a saddle or seat for the human body, wherein said first component or support component comprises a first discoidal base, able to come into contact and to be associated or constrained to said second component, and a second annular base, opposite to said discoidal base, wherein said discoidal base and said second annular base are connected by a substantially tubular wall, comprising a through opening having a substantially circular section, the extension of which involves at least said annular base, wherein said wall constitutes a recessed area with respect to said annular base and/or said discoidal base, adapted in use to house, for example, a rear portion of a fork of a bicycle saddle, and/or wherein said second component has a substantially hemispherical conformation, provided with a hemispherical cap and a flat base.

23. An apparatus for making a support element for a human body, including a saddle for a bicycle or a vehicle, a grip for a handlebar of a bicycle or a vehicle, a shock-absorbing or suspension element for a saddle or seat for the human body, wherein said support element comprises a first component or support component and a second component or padding component which is constrained to said first component or support component, wherein said second component or padding component comprises a honeycombed structure comprising a plurality of cells, each cell comprising branches or sections and vertices, wherein each cell of said plurality of cells has a polyhedral or parallelogram shape, said apparatus comprising:

means for detecting a pressure exerted by at least one anatomical part of the human body of a user on a test element, said detection means being designed to generate a plurality of output signals;

means for processing and/or translating said plurality of output signals into a first data series defining a pressure map associated with the pressure exerted by said at least one anatomical part of the human body of said user on said test element, wherein said first data series comprises a series of colour shades, from white and/or grey to black, corresponding to increasing pressure values;

means for transforming said first data series into a second data series to obtain a three-dimensional digital file of said support element, for example wherein said second data series comprises information relating to and/or defines a position, density and/or conformation of each cell of said plurality of cells and/or on a thickness of said branches or sections and vertices of each cell of said second component or padding component, and/or the type and/or shape of said support element;

means for three-dimensional printing of said second component or padding component on the basis of information present in said three-dimensional digital file, wherein said three-dimensional printing means comprise a three-dimensional printing of the "Digital Light Synthesis" or DLS type, or of the DLP or "Digital Light Processing" type or of the FDM or "Fused Deposition Modeling" type or MJF or "Multi Jet fusion" type or SLS or "Selective Laser Sintering" type, means designed to acquire or store data of other users and means for comparing said first data series with said data of other users contained or stored in a ad hoc database, such as for example a cloud storage system, so as to attribute a certain meaning to said first data series, wherein said meaning includes the definition of a category for the user, wherein said category includes data and/or files of other users who present a similar or analogous response to said first data series.

24. The apparatus according to claim 23, wherein said detection means comprise a plurality of pressure sensors positioned on said test element or wherein said processing and/or translation means comprise a first computerized logic unit with at least a first computer program or software configured to process and/or translate the plurality of signals obtained by said detection means so as to generate said first data series.

25. The apparatus according to claim 23, wherein said transformation means comprises a second computerized logic unit with at least one second computer program or software configured to translate said first data set into said second data set.

26. The apparatus according to claim 23, wherein said data of other users are personal data such as age, sex, weight, height, build, posture and data related to the mode/preference of execution of the athletic or pedalling gesture, such as pedalling style, running style, posture on the bicycle or vehicle, the type of performance to be carried out.

27. The apparatus according to claim 23, wherein said comparing means comprises at least a third computer program or software stored in said first or second computerized logic unit, said third computer program or software being configured to associate or couple said first data series with said data and/or files of other users presenting a similar or analogous response to said first data series.

* * * * *